(12) United States Patent
Goto et al.

(10) Patent No.: US 11,478,473 B2
(45) Date of Patent: Oct. 25, 2022

(54) SLEEP IMPROVING AGENT

(71) Applicants: AMINO UP CO., LTD., Sapporo (JP);
OTSUKA PHARMACEUTICAL CO., LTD., Tokyo (JP)

(72) Inventors: Kazunori Goto, Sapporo (JP); Jun Nakahigashi, Sapporo (JP); Atsuya Sato, Sapporo (JP); Yosuke Hirayama, Sapporo (JP); Moeri Horikoshi, Sapporo (JP); Noriyuki Kouda, Osaka (JP); Syoichiro Inoue, Osaka (JP); Ikutaro Sato, Osaka (JP); Manami Kato, Osaka (JP)

(73) Assignees: Amino Up Co., Ltd., Sapporo (JP); Otsuka Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 16/839,889

(22) Filed: Apr. 3, 2020

(65) Prior Publication Data

US 2020/0246335 A1 Aug. 6, 2020

Related U.S. Application Data

(62) Division of application No. 16/303,960, filed as application No. PCT/JP2017/019644 on May 26, 2017, now abandoned.

(30) Foreign Application Priority Data

May 26, 2016 (JP) .................... 2016-105477

(51) Int. Cl.
*A61K 31/4985* (2006.01)
*A61P 25/20* (2006.01)
*A61P 25/22* (2006.01)

(52) U.S. Cl.
CPC .......... *A61K 31/4985* (2013.01); *A61P 25/20* (2018.01); *A61P 25/22* (2018.01)

(58) Field of Classification Search
CPC ....... A61K 31/4985; A61P 25/20; A61P 25/22
See application file for complete search history.

(56) References Cited

U.S. PATENT DOCUMENTS

| 7,202,279 | B1 | 4/2007 | Kozikoqaki et al. | |
|---|---|---|---|---|
| 2003/0212133 | A1* | 11/2003 | Bryans | A61P 25/20 514/561 |
| 2006/0258663 | A1 | 11/2006 | Brimble et al. | |
| 2007/0161640 | A1 | 7/2007 | Kozikowski et al. | |
| 2013/0085141 | A1 | 4/2013 | Li et al. | |
| 2016/0159858 | A1 | 6/2016 | Suzuki et al. | |
| 2019/0201395 | A1 | 7/2019 | Goto et al. | |

FOREIGN PATENT DOCUMENTS

| JP | 2003-525850 A | 9/2003 |
|---|---|---|
| JP | 2007/504235 A | 3/2007 |
| JP | 2013138631 A * | 7/2013 |
| JP | 5690028 B1 | 3/2015 |
| WO | WO 03104441 A2 * | 12/2003 |
| WO | 2011/077760 A1 | 6/2011 |
| WO | WO 2011077760 A1 * | 6/2011 |
| WO | 2012/043808 A1 | 4/2012 |
| WO | 2013/047055 A | 4/2013 |
| WO | 2015/013397 A2 | 1/2015 |

OTHER PUBLICATIONS

English translation of JP 2013138631 A, publ. 2013 (Year: 2013).*
CAS STN Abstract (RN 4549-02-4) (Year: 2003).*
Pastukhov, I., et al., "Chaperone Hsp70 Is Involved in the Molecular Mechanisms of Slow Wave Sleep Regulation", Doklady Biochemistry and Biophysics, 2015, vol. 461, pp. 76-79 (4 pages).
International Preliminary Report on Patentability and Translation of Written Opinion, dated Dec. 6, 2018 from the International Bureau in counterpart International application No. PCT/JP2017/019644.
Ekimova, I., "Somnogenic Effect of Exogenous Heat Shock Protein 70 kDa Is Mediated by GABA(A) Receptors in the Preoptic Area of the Hypothalamus", Doklady Biological Sciences, 2013, vol. 449, pp. 89-92 (4 pages).
International Search Report, dated Jun. 27, 2017 from the International Bureau in counterpart International application No. PCT/JP2017/019644.
Extended European Search Report dated Jan. 9, 2020 in European Application No. 17802907.0.
Ito, Tomohiro, et al., "Enzyme-Treated Asparagus Extract Promotes Expression of Heat Shock Protein and Exerts Antistress Effects", Journal of Food Science, vol. 79, No. 3, 2014, pp. H413-H419 (7 pages).
Hsu, C-C., et al., "Association of L-Glutamic Acid Decarboxylase to the 70-kDa Heat Shock Protein as a Potential Anchoring Mechanism to Synaptic Vesicles", The Journal of Biological Chemistry, vol. 275, No. 27, Issue of Jul. 7, 2000, pp. 20822-20828 (8 pages).
Li et al., "Identification of Antifungal Compounds Produced by *Lactobacillus casei* AST18", Current Microbiology, 2012, vol. 65, No. 2, pp. 156-161 (6 pages total).

(Continued)

*Primary Examiner* — Sarah Pihonak
(74) *Attorney, Agent, or Firm* — Sughrue Mion, PLLC

(57) ABSTRACT

The present invention provides a heat shock protein expression-inducing agent, more specifically, a heat shock protein expression-inducing agent comprising a compound represented by formula (I):

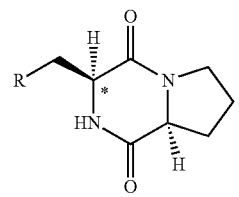

wherein R is a lower alkyl, phenyl, or hydroxyphenyl, or a salt thereof.

2 Claims, 4 Drawing Sheets

Specification includes a Sequence Listing.

(56) References Cited

OTHER PUBLICATIONS

Cornacchia, C., et al., "2,5-Diketopiperazines as Neuroprotective Agents", Mini-Reviews in Medicinal Chemistry, 2012, vol. 12, No. 1, pp. 2-12 (11 pages).

Zhong, J-M., et al., "Antidepressant effect of geranylgeranylacetone in a chronic mild stress model of depression and its possible mechanism", Experimental and Therapeutic Medicine, vol. 4, 2012, pp. 627-632 (6 pages).

Kumar et. al., Appl Biochem S Biotechnology, 2014, Springer, vol. 173, pp. 116-128 (Year: 2014).

Chen et. al., Journal of Food Science, 2009, The Soc for Food Sci & Tech, vol. 74(2), pp. C100-C105 (Year: 2009).

Manami KATO et al., "Effects of food containing asparagus extract (ONR-8) on alertness upon awakening and sleep quality on Monday in healthy participants with a discrepancy between the sleep-wake rhythm on workdays and weekends", Jpn Pharmacol Ther, 2016, vol. 44, No. 5, pp. 743-750 (6 pages total).

Tomohiro Ito et al., "Effects of enzyme-treated asparagus extract on heat shock protein 70, stress indices, and sleep in healthy adult men", J Nutr Sci Vitaminol, 2014, vol. 60, pp. 283-290 (8 pages total).

Jun Takanari et al., "Effect of enzyme-treated asparagus extract (ETAS) on psychological stress in healthy individuals", J Nutr Sci Vitaminol, 2016, vol. 62, pp. 198-205 (8 pages total).

Luigi Brunetti et al., "Synthesis and neuromodulatory effects of TRH-related peptides; inhibitory activity on catecholamine release in vitro", Pharmacological Reports, 2013, vol. 65, pp. 823-835 (13 pages total).

Heather A. Mitchell et al., "Good night and good luck: Norepinephrine in sleep pharmacology", Biochemical Pharmacology, 2010, vol. 79, pp. 801-809 (9 pages total).

\* cited by examiner

[Figure 1]
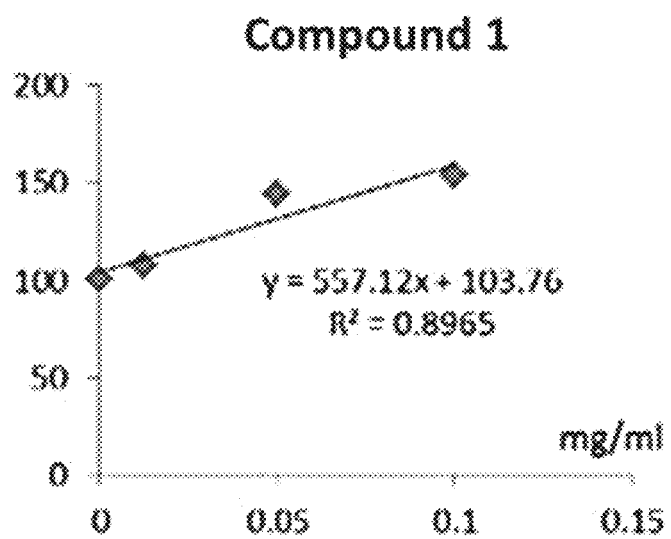
[Figure 2]
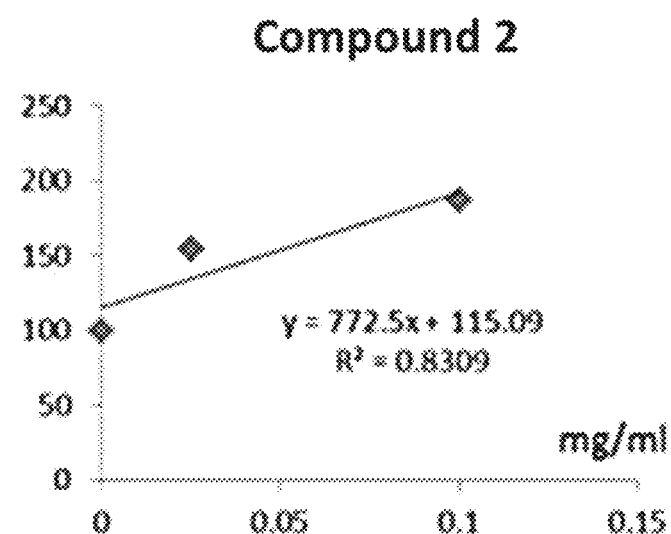

[Figure 3]
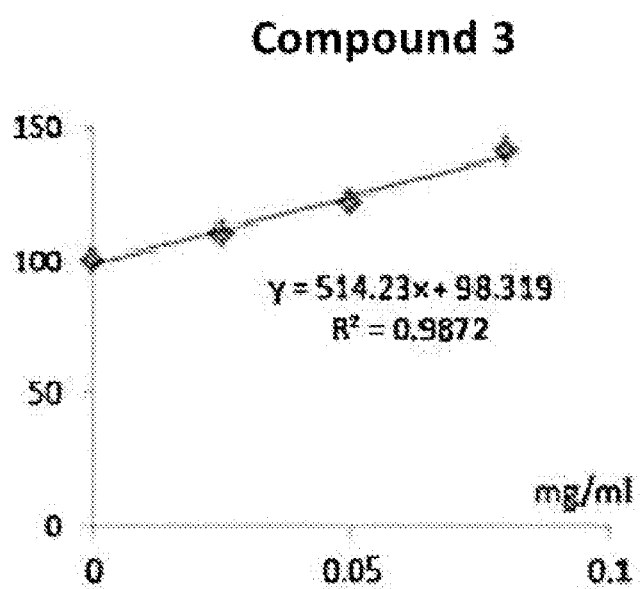

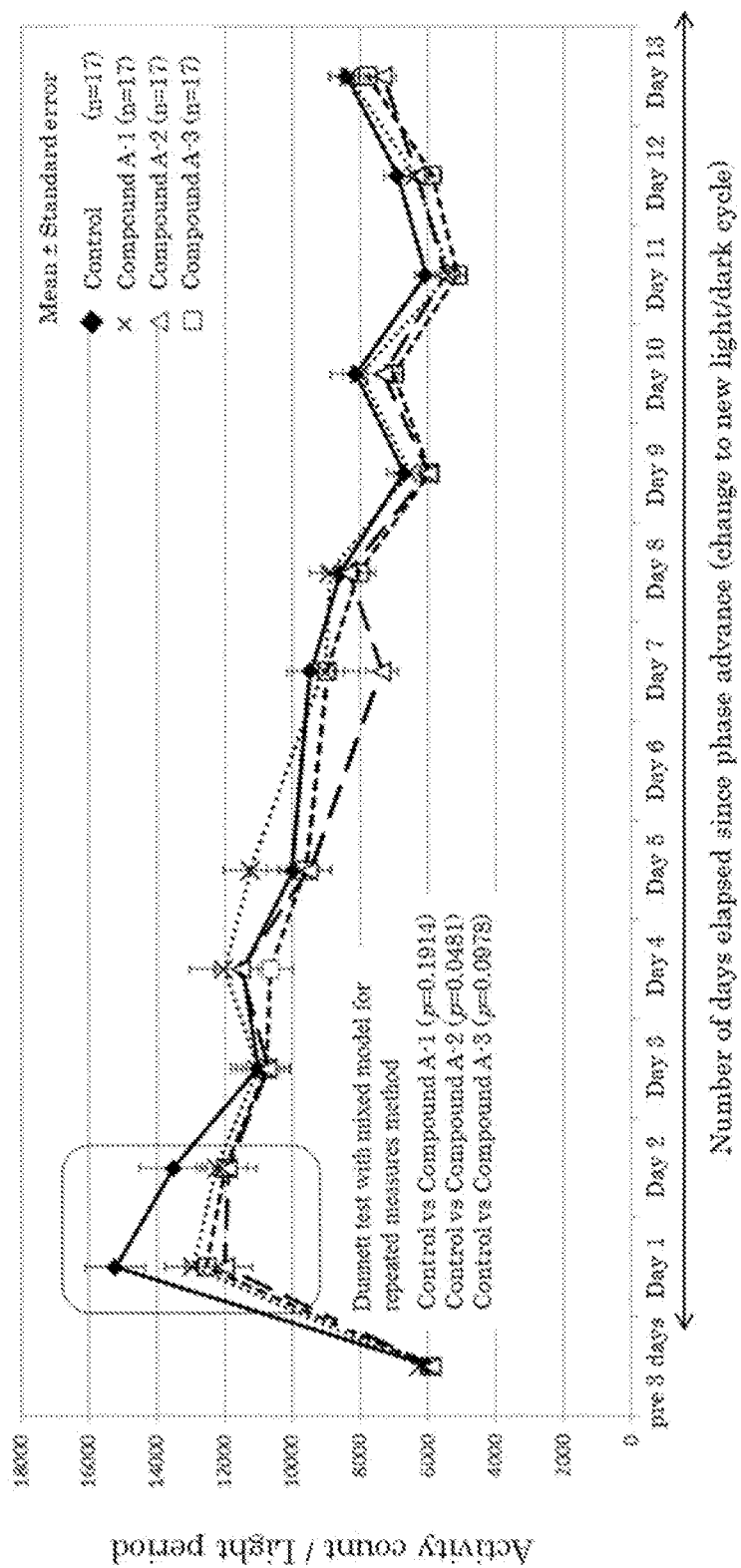
Figure 4. Transition of activity level in the light period after phase advance

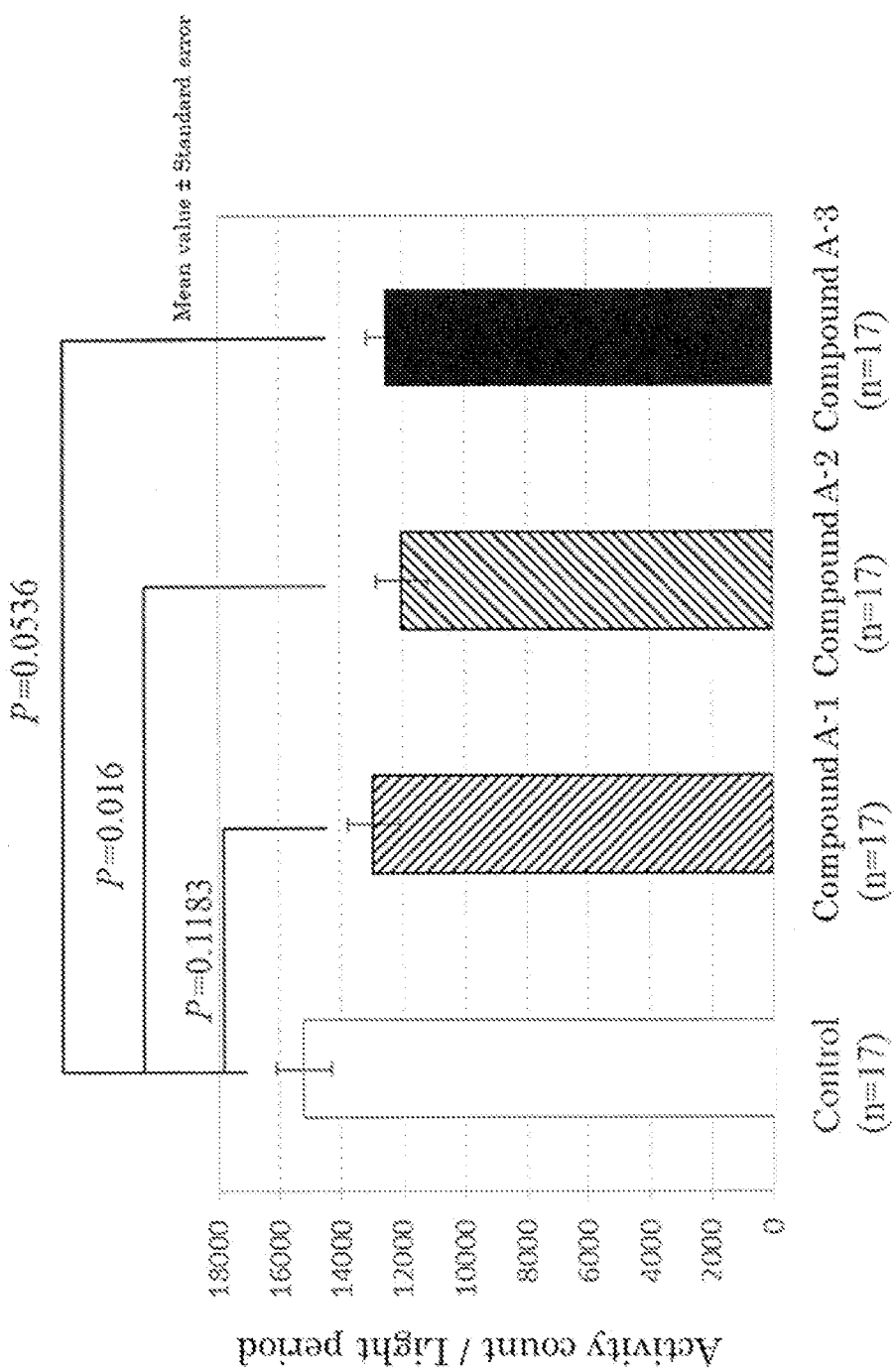
Figure 5. Activity level on Day 1, light period (12 hours) after phase advance
P values show the results of Dunnett test.

SLEEP IMPROVING AGENT

CROSS REFERENCE TO RELATED APPLICATIONS

This application is a divisional of application Ser. No. 16/303,960 filed Dec. 27, 2018, which is a National Stage of International Application No. PCT/JP2017/019644 filed May 26, 2017, claiming priority based on Japanese Patent Application No. 2016-105477 filed May 26, 2016.

TECHNICAL FIELD

The present application is filed claiming the priority of the Japanese Patent Application No. 2016-105477, the entire contents of which are herein incorporated by reference.

The present invention relates to a heat shock protein expression-inducing agent, sleep improving agent, anti-stress agent and autonomic nerve-adjusting agent.

BACKGROUND ART

Organisms have various defense mechanisms to adapt to the growth environment. For example, when the growth temperature increases by 5-10° C., the three-dimensional structure of cellular proteins starts to change by thermal denaturation. A group of proteins called "chaperones" is known to involve in the mechanism for repairing this change. Heat shock proteins (hereinafter also referred to as "HSPs") are known as representative proteins that have a chaperone function. In mammals, more than ten kinds of HSPs have been currently reported and classified into HSP 20 family, HSP 10 family, HSP 70 family, HSP 90 family, and the like on the basis of the molecular weight thereof.

HSPs are also called stress proteins, of which the expression is enhanced in vivo in response to environmental stress, pathological stress, psychological stress and the like. HSPs expressed in vivo have the following role: to bind specifically to proteins that have lost their original physiological functions because of a partial change of the higher-order structure thereof under various stress, and utilize energy generated by hydrolysis of ATP to return the higher-order structure of the binding partner protein to its original structure, and restore the physiological function of the protein.

Thus, HSPs contribute to biological defense and maintaining homeostasis of living bodies. If HSP expression can be induced in vivo, it will be effective in preventing or ameliorating various diseases and symptoms caused by abnormality of higher-order structure of proteins or various diseases and symptoms related to HSPs.

Among HSPs, HSP70 has been actively studied in particular. In recent years, the relationship of HSP70 with sleep (Non-patent Documents 1 and 2) or stress (Non-patent Documents 3 and 4) has become clear. It is also known that there is a close relationship between stress and autonomic nervous disorders. Therefore, the chaperone function of HSP 70 is considered to contribute to recovery from damages such as sleep deprivation, daily stress, autonomic neuropathy and the like.

For this reason, HSP70 expression-inducing substances have been researched in order to apply them to pharmaceuticals, quasi-drugs, and the like. As such a substance, for example, Zerumbone, etc. have been reported (Patent Document 1).

CITATION LIST

Patent Documents

Patent Document 1: WO 2012/043808

Non-Patent Documents

Non-Patent Document 1: Doklady Biological Sciences, 2013, Vol. 449, pp. 89-92

Non-Patent Document 2: Doklady Biological Sciences, 2015, Vol. 461, pp. 76-79

Non-Patent Document 3: Exp. Ther. Med. 2012, Oct; 4(4), 627-632

Non-Patent Document 4: J. Biol. Chem. 2000, Vol. 275, No. 27, 20822-20828

SUMMARY OF INVENTION

Technical Problem

The object of the present invention is to provide a HSP expression-inducing agent, sleep improving agent, anti-stress agent, autonomic nerve-adjusting agent or the like, comprising an active ingredient having an excellent HSP expression inducing activity.

Solution to Problem

As a result of intensive studies to attain the above object, the present inventors have found that a proline-containing 3-alkyl diketopiperazine represented by the following general formula (I) or a salt thereof has an excellent HSP expression-inducing activity, and based thereon, it shows sleep improving activity, anti-stress activity, autonomic nerve-adjusting activity and the like. The present invention has been accomplished on the basis of these findings.

The present invention includes the following embodiments.

[1] A heat shock protein expression-inducing agent comprising a compound represented by formula (I):

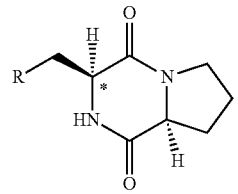

wherein R is a lower alkyl, phenyl, or hydroxyphenyl, or a salt thereof.

[2] The heat shock protein expression-inducing agent according to [1], wherein R is isopropyl, phenyl, or hydroxyphenyl.

[3] The heat shock protein expression-inducing agent according to [1], wherein R is isopropyl.

[4] The heat shock protein expression-inducing agent according to any of [1]-[3], which is in the form of a pharmaceutical composition, quasi-drug composition or food and beverage composition.

[5] A sleep improving agent comprising a compound represented by formula (I):

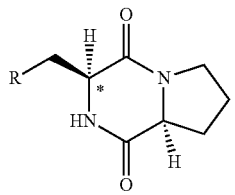

wherein R is a lower alkyl, phenyl, or hydroxyphenyl, or a salt thereof.

[6] The sleep improving agent according to [5], wherein R is isopropyl, phenyl, or hydroxyphenyl.

[7] The sleep improving agent according to [5], wherein R is isopropyl.

[8] The sleep improving agent according to any of [5]-[7], which is in the form of a pharmaceutical composition, quasi-drug composition or food and beverage composition.

[9] An autonomic nerve-adjusting agent comprising a compound represented by formula (I):

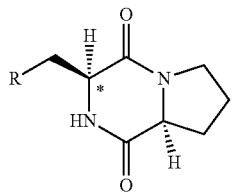

wherein R is a lower alkyl, phenyl, or hydroxyphenyl, or a salt thereof.

[10] The autonomic nerve-adjusting agent according to [9], wherein R is isopropyl, phenyl, or hydroxyphenyl.

[11] The autonomic nerve-adjusting agent according to [9], wherein R is isopropyl.

[12] The autonomic nerve-adjusting agent according to any of [9]-[11], which is in the form of a pharmaceutical composition, quasi-drug composition or food and beverage composition.

[13] An anti-stress agent comprising a compound represented by formula (I):

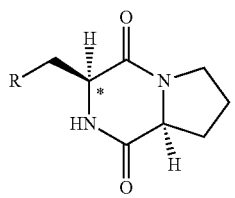

wherein R is a lower alkyl, phenyl, or hydroxyphenyl, or a salt thereof.

[14] The anti-stress agent according to claim 13, wherein R is isopropyl, phenyl, or hydroxyphenyl.

[15] The anti-stress agent according to claim 13, wherein R is isopropyl.

[16] The anti-stress agent according to any of any of [13]-[15], which is in the form of a pharmaceutical composition, quasi-drug composition or food and beverage composition.

Effect of Invention

According to the pharmaceutical composition of the present invention, it is possible to provide a HSP expression-inducing agent, sleep improving agent, anti-stress agent, autonomic nerve-adjusting agent and the like, which has one or more functions or effects described below:
(1) inducing the expression of HSP70,
(2) improving the quality of sleep, specifically one or more followings: sleep quality, sleep-awakening rhythm, deep sleep feeling, feeling when waking up, feeling tired when getting up, sleepiness during the day, work efficiency, gloomy feeling resulting from unsatisfactory sleep, and the like,
(3) anti-stress activity,
(4) autonomic nerve-adjusting activity,
(5) others, preventing or ameliorating various diseases and symptoms caused by abnormality of higher-order structure of proteins or various diseases and symptoms related to HSPs.

BRIEF DESCRIPTION OF THE DRAWINGS

FIG. 1 is a figure showing an HSP70 mRNA expression level by a proline-containing 3-alkyl diketopiperazine (Compound 1).

FIG. 2 is a figure showing a HSP70 mRNA expression level by a proline-containing 3-alkyl diketopiperazine (Compound 2).

FIG. 3 is a figure showing a HSP70 mRNA expression level by a proline-containing 3-alkyl diketopiperazine (Compound 3).

FIG. 4 shows the transition of activity level of rats in the light period after the phase advance.

FIG. 5 is a figure showing the activity level of rats on Day 1, light period (12 hours) after the phase advance.

DESCRIPTION OF EMBODIMENTS

The HSP expression-inducing agent according to the present invention comprises a proline-containing 3-alkyl diketopiperazine represented by general formula (I):

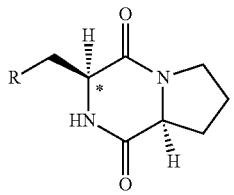

wherein R is a lower alkyl, phenyl, or hydroxyphenyl, or a salt thereof as an active ingredient.

The "lower alkyl" in the above formula (I) means a linear or branched alkyl group having 1-6 carbon atoms. Specific examples thereof include methyl, ethyl, propyl, isopropyl, butyl, isobutyl, sec-butyl, tert-butyl, pentyl, neopentyl, hexyl, isohexyl and the like. Preferred is a linear or branched alkyl group having 1-4 carbon atoms such as isopropyl.

In the above formula (I), R is a lower alkyl, phenyl, or hydroxyphenyl, preferably isopropyl, phenyl, or hydroxyphenyl, particularly preferably isopropyl.

Among the proline-containing 3-alkyl diketopiperazine of the above formula (I), particularly preferred are the following Compounds 1-3 (particularly, Compound 1).

(Compound 1)
Name: (3S, 8aS)-3-isobutylhexahydropyrrolo[1,2-a]pyrazine-1,4-dione
Abbreviated name: Cyclo(L-Leu-L-Pro)

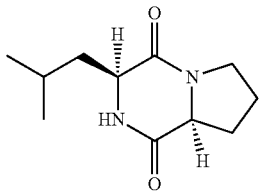

(Compound 2)
Name: (3S, 8aS)-3-benzylhexahydropyrrolo[1,2-a]pyrazine-1,4-dione
Abbreviated name: Cyclo(L-Phe-L-Pro)

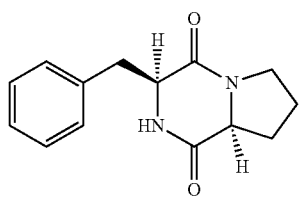 [SMILES: O=C1N[C@@H](Cc2ccccc2)C(=O)N2CCC[C@@H]12]

(Compound 3)
Name: (3S, 8aS)-3-(4-hydroxybenzyl)hexahydropyrrolo[1,2-a]pyrazine-1,4-dione
Abbreviated name: Cyclo(L-Tyr-L-Pro)

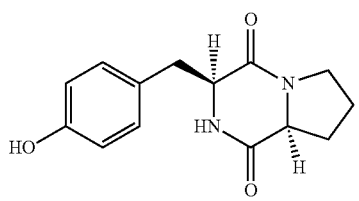 [SMILES: O=C1N[C@@H](Cc2ccc(O)cc2)C(=O)N2CCC[C@@H]12]

Salts of the proline-containing 3-alkyl diketopiperazine include those acceptable in the field of pharmaceuticals or foods and beverages, for example, salts with inorganic bases, salts with organic bases, salts with basic amino acids, etc.

Suitable examples of salts with inorganic bases include, for example, alkali metal salts such as sodium salt, potassium salt and the like; alkaline earth metal salts such as calcium salt, magnesium salt and the like; ammonium salt and the like.

Suitable examples of salts with organic bases include, for example, salts with alkylamines (trimethylamine, triethylamine and the like), heterocyclic amines (pyridine, picoline and the like), alkanolamines (ethanolamine, diethanolamine, triethanolamine and the like), dicyclohexylamine, N,N'-dibenzylethylenediamine, or the like.

Preferable examples of salts with basic amino acids include, for example, salts with arginine, lysine, ornithine, or the like.

Among these salts, alkali metal salts or alkaline earth metal salts are preferable, and sodium salt is particularly preferable.

The proline-containing 3-alkyl diketopiperazine or a salt thereof used in the present invention can be prepared according to a method known in the art, for example, a chemical synthesis method, an enzymatic method, a microorganism fermentation method, or the like. Specifically, the compound can be synthesized by subjecting a linear peptide to dehydration/cyclization reaction, for example, according to a method shown in JP 2003-252896 A or J. Peptide Sci., 10, 737-737(2004).

In addition, the above-mentioned Compounds 1-3 are known compounds, and thus can be obtained, for example, from BACHEM.

In the present invention, the above proline-containing 3-alkyl diketopiperazine or a salt thereof may be used. alone or in combination of two or more kinds thereof, as an active ingredient. For example, one of the Compounds 1-3 may be used. alone, or two or three of them may be used together.

For instance, when two of the Compounds 1-3 are used, the usage ratio is not particularly limited. When two kinds of Compounds 1 and 2, are used, the ratio thereof is, for example, Compound 1: Compound 2=10-0.5:3-0.1, preferably 6-1:2-0.5. When two kinds of Compounds 1 and 3 are used, the ratio thereof is, for example, Compound 1:Compound 3=10-0.5:5-0.5, preferably 6-1:4-0.7. When two kinds of Compounds 2 and 3 are used, the ratio thereof is, for example, Compound 2:Compound 3=3-0.1:5-0.5, preferably 0.5:4-0.7.

In addition, for instance, when all (three) kinds of the Compounds 1-3 are used, the usage ratio is not particularly limited, but include, for example, Compound 1:Compound 2 :Compound 3=10-0.5:3-0.1:5-0.5, preferably 6-1:2-0.5:4-0.7.

The proline-containing 3-alkyl diketopiperazine or a salt thereof has an excellent HSP expression-inducing activity. Therefore, the HSP expression-inducing agent of the present invention is effective in preventing or ameliorating various diseases and symptoms caused by abnormality of the higher-order structure of proteins or various diseases and symptoms related to HSPs.

In the present invention, HSPs of which the expression is induced include any of SP20 family proteins such as HSP20, HSP27, and HSP28; HSP40 family proteins such as HSP40 and HSP47; HSP70 family proteins such as HSP70, HSP72, and SP73; HSP90 family proteins such as HSP90a and HSP90b. Preferred are HSP70 family proteins, and more preferred is HSP70.

In the present invention, the induction of expression of HSPs includes expression in vivo and in vitro, preferably expression in vivo. The in vivo site where the expression of HSP is induced is preferably within the brain.

The proline-containing 3-alkyl diketopiperazine or a salt thereof shows an excellent sleep improving activity, anti-stress activity, autonomic nerve-adjusting activity, and the like, on the basis of its HSP expression-inducing activity.

Therefore, the present invention provides a sleep improving agent, anti-stress agent, autonomic nerve-adjusting agent, and the like, comprising the proline-containing 3-alkyl diketopiperazine or a salt thereof as an active ingredient.

The "sleep improving" in the present invention means that improved effects on one or more followings: sleep quality, sleep-awakening rhythm, deep sleep feeling, feeling when waking up, feeling tired when getting up, sleepiness during the day, work efficiency, gloomy feeling resulting from unsatisfactory sleep, and the like are observed.

The "improving the quality of sleep" means to obtain a good quality of sleep is obtained by shortening the sleeping latency, decreasing the number and time of arousal during sleep, and smoothing the transition to slow-wave sleep which is regard as deep sleep after sleep onset to increase sleep time.

The "improving sleep-awakening rhythm" means to improve the shift of sleep-awakening rhythm or to adjust sleeping/waking up rhythm. The shift of sleep-awakening rhythm also includes social jet lag where social time and biological clock do not match. The social jet lag is caused by a night-time light environment and a big change of working environment, etc., that is, it means that bedtime/wakeup rhythm shifts on weekdays with social restrictions such as work and on holidays without restrictions, or the circadian rhythm of the living body collapses due to irregular sleep cycles and the like.

By improving sleep quality and/or sleep-awakening rhythm, deep sleep feeling that you can sleep soundly and a refresh feeling when waking up can be obtained. Furthermore, the work efficiency rises without feeling sleepiness during the day or feeling tired when getting up. Also, it is possible to reduce sleeping feeling caused by not getting a good quality sleep or shifting a sleeping/waking up rhythm.

The improvement effect means improvement of symptoms or conditions, prevention or delay of deterioration of symptoms or conditions, or reversal, prevention or delay of the progress of symptoms.

The "anti-stress activity" in the present invention means an activity capable of preventing fatigue caused by stress in a mammal, particularly human, or preventing fatigue due to stress in the brain. Here, fatigue is a phenomenon in which physical and mental performance temporarily declines, when a physical or mental load is given consecutively. The decline of performance is a qualitative or quantitative decline in physical and mental abilities.

The "autonomic nerve-adjusting activity" in the present invention means to improve a disturbance in the balance of sympathetic and parasympathetic balance (autonomic nervous balance) caused by excessive stress burden, decreased level of autonomic nervous activity, and the like. For example, since the function of the gastrointestinal tract is mainly dominated by the parasympathetic sensory nerve, if the sympathetic tension is maintained by a stress load, the action of the gastrointestinal tract is suppressed, thereby causing gastrointestinal disorders such as anorexia and constipation. In addition, it is considered that insomnia is caused when the parasympathetic nerve does not function well due to a stress load and the activity of the sympathetic nerve is continued to accelerate. While there is a close relationship between stress and autonomic nervousness as described above, there is also autonomic nervous disorder not due to stress load. Stress load does not necessarily cause autonomic nervous disorders, but may induce other physical symptoms.

In the present invention, the proline-containing 3-alkyl diketopiperazine or a salt thereof can be used as it is as a HSP expression-inducing agent, sleep improving agent, anti-stress agent, autonomic nerve-adjusting agent, or the like (hereinafter referred to as "HSP expression-inducing agent or the like"). Also, it can be used in combination with carriers that can be added to pharmaceuticals or quasi-drugs, or food additives, to the extent that they do not affect the intended function or effect.

In the present invention, the proline-containing 3-alkyl diketopiperazine or a salt thereof can be added to various pharmaceuticals, quasi-drugs, foods and beverages as a HSP expression-inducing agent, and thus used in the form of pharmaceutical compositions, quasi-drug compositions, food and beverage compositions and the like.

The pharmaceuticals, quasi-drugs, foods and beverages are not particularly limited as long as they are usually used, and examples thereof include tablets, granules, capsules, powders, chewable tablets, confectioneries (cookies, biscuits, chocolate confectionery, chips, cake, gum, candy, gummi, sweet buns, sweet jellied adzuki-bean paste, pudding, jelly, yogurt, ice cream, sherbet and the like), breads, noodles, rice, cereal foods, beverages (liquid, soft drinks, carbonated drinks, nutritional drinks, powdered drinks, fruit drinks, milk drinks, jelly drinks and the like), soups (powder soups, freeze-dried soups), miso soups (powder miso soups, freeze-dried miso soups) and the like.

In addition, foods and beverages include foods with function claims, foods for specified health uses, health food, nutritional supplements (supplements), foods for medical use and the like.

The subjects to be applied by the HSP expression-inducing agent or the like in the present invention are not particularly limited, but include, for example, subjects who have subjective dissatisfaction with sleeping feeling such as shallow asleep, insufficient sleep feeling when getting up, poor sleep, insufficient deep sleep feeling (cannot sleep deeply), bad dreaming, unrecovered fatigue, and the like; subjects who have no subjective complaints about sleeping feeling, but want to improve sleep quality because they are feeling fatigue; subjects who feels disorder of autonomic nerve; and subjects who are stressed in everyday life; and the like. Also, subjects with no particular problem can take up the agent daily for the purpose of maintaining good sleep, preventing sleep disorders, improving sleep quality, autonomic nerve-adjusting activity, anti-stress activity and the like.

The subjects to which the present invention applies are especially humans. The present invention is also applicable to mammals other than humans (e.g., mouse, rat, hamster, monkey, cow, horse, pig, sheep, goat, dog, cat, guinea pig, rabbit and the like).

In the HSP expression-inducing agent or the like of the present invention, the daily dose (intake) of the proline-containing 3-alkyl diketopiperazine or a salt thereof is not particularly limited and it may be set as appropriate according to the purpose of administration (target disease and symptom), administration form, sex, weight and age of subject, etc., but is usually 0.1 µg-1.7 g as a proline-containing 3-alkyl diketopiperazine in the case of a human adult, preferably 1 µg-1.5 g, and more preferably 5 µg-1.3 g.

In the case of a human adult, the daily dose of Compound 1 is usually 0.5 µg-500 mg, preferably 1 µg-450 mg, more preferably 10 µg-400 mg.

In the case of a human adult, the daily dose of Compound 2 is usually 0.1 µg-400 mg, preferably 2 µg -350 mg, more preferably 5 µg-300 mg.

In the case of a human adult, the daily dose of Compound 3 is usually 0.1 µg-800 mg, preferably 2 µg-700 mg, more preferably 5 µg-600 mg.

The timing of administration of the HSP expression-inducing agent or the like of the present invention is not particularly limited, but it is preferably administered (consumed) once a day before going to bed.

In addition, the present invention provides the proline-containing 3-alkyl diketopiperazine or a salt thereof for use as a HSP expression-inducing agent, sleep improving agent, anti-stress agent, autonomic nerve-adjusting agent, or the like.

Also, the present invention provides use of the proline-containing 3-alkyl diketopiperazine or a salt thereof for the preparation of a HSP expression-inducing agent, sleep improving agent, anti-stress agent, autonomic nerve-adjusting agent, or the like.

Furthermore, the present invention provides a method for inducing HSP expression, improving sleep, anti-stressing, adjusting autonomic nerve, or the like, which comprises administrating the proline-containing 3-alkyl diketopiperazine or a salt thereof to a subject.

In these embodiments, the definitions of the terms, the proline-containing 3-alkyl diketopiperazine or a salt thereof, the form of use, the subject, the dosage, the timing of administration, the blending amount in each agent, etc. are the same as described above.

EXAMPLES

Hereinafter, the present invention will be described in more detail with reference to representative examples, but the present invention is not limited to the following examples. Unless otherwise specified, "%" means "wt %".

Example 1

Evaluation of HSP70 mRNA Expression-Inducing Activity

The HSP70 expression-inducing activity by Compounds 1-3 was evaluated by measuring a HSP70 mRNA expression level.

Human promyelocytic leukemia cells (HL-60 cells) was suspended in RPMI 1640 medium supplemented with 10% fetal bovine serum, and was transferred into a 1.5 mL tube (45,000 cells/0.9 mL). To the tube was added 0.1 mL of each sample that had been prepared in a 1% DMSO solution and the tube was allowed to stand at 37° C. for 4 hours. To a control was added 0.1 mL of 1% DMSO solution. After cultured for 4 hours, the cells was centrifuged by a small refrigerated centrifuge (1,000 g×5 minutes) to precipitate the HL-60 cells. After removal of the supernatant, the cells were lysed in 0.25 mL Trizol (manufactured by Thermo Fisher Scientific) and then total RNA was extracted according to the protocol. The RNA was dissolved in RNase-free water, and the concentration of the RNA (wave length 260 nm) was measured by using a microvolume spectrophotometer Nano-Drop2000/2000c (manufactured by Thermo Fisher Scientific). The RNA solution was diluted with RNase-free water so as to have a concentration of 50 ng/mL, and then cDNA was synthesized by using ReverTra Ace$^{(R)}$ qPCR RT Kit (manufactured by TOYOBO). The reaction liquid (10 μl) after the reverse transcription was diluted with RNase-free water so as to be 100 μL, and then used as a template for PCR. Beta 2 microglobulin gene was used as an internal control gene for correction of the HSP70 gene expression. The primer sequences of genes used for the PCR reaction are as follows.

```
HSP70 forward primer:
                                    (SEQ ID NO: 1)
GCATTTCCTAGTATTTCTGTTTGT HSP70 reverse primer:
                                    (SEQ ID NO: 2)
AATAGTCGTAAGATGGCAGTATA Beta 2 microblobulin forward primer:
                                    (SEQ ID NO: 3)
TAGCTGTGCTCGCGCTACT Beta 2 microblobulin reverse primer:
                                    (SEQ ID NO: 4)
AGTGGGGGTGAATTCAGTGT
```

The expression was analyzed by using CFX Connect Real-Time PCR Detection System (manufactured by Bio-rad). 10 μL of the PCR reaction liquid was incubated at 95° C. for 3 minutes (initial denaturation), followed by repetition of 55 cycles comprising denaturation at 95° C. for 10 seconds, and annealing and extension at 57.8° C. for 30 seconds. Finally, the melting curve was measured every 0.2° C. in the range from 65° C. to 95° C. Expression levels of HSP70 gene and internal standard gene were analyzed using Bio-Rad CFX Manager 3.1.

The abilities of inducing HSP70 mRNA expression of Compounds 1, 2, and 3 are shown in FIGS. 1-3 by percentages for the control, respectively. From these results, it was revealed that each sample enhanced mRNA expression of HSP70 gene as compared with the control. In addition, concentration dependence of each active ingredient on HSP70 mRNA expression inducing ability was investigated. As a result, the concentrations at which HSP70 mRNA expression inducing ability was increased up to 150% relative to the control were 0.083 mg/ml for Compound 1, 0.045 mg/ml for Compound 2, and 0.101 mg/ml for Compound 3.

Example 2

Firstly, 7-week old male Wistar rats were implanted intraperitoneally with a small activity meter (NanoTag (R), Kissei Comtech Co., Ltd.). Subsequently, after a week of recovery period, the rats were divided into four groups (Control group, Compound A-1 group, Compound A-2 group, and Compound A-3 group; n=17 each) shown in Table 1 by stratified randomization assignment using body weight as an index, and test diets were dietary administered to them. At the 15th day from the start of dietary administration, the light/dark cycle was advanced by 8 hours, and after that, dietary administration of test diets was continued for 2 weeks. The light/dark cycle of the breeding environment excluding the phase advance date was set to 12 hours cycle, and the illuminance of the light period was set to be approximately 200 1x(185-230 1x). In this model of mild sleep disorder with the phase advance, the influence of test feed administration on the light period activity level after the phase advance was examined.

The test was carried out by a two-sided test, the significance level of the test was set to 5%, and the trend difference was 10% on both sides. For the analysis, SAS software release 9.3 (manufactured by SAS Institute Japan Ltd.) was used.

TABLE 1

| Group (n = 17) | Test diet |
|---|---|
| Control | MF |
| Compound A-1 | MF containing 0.0005% of Compound A (Equivalent to 0.62 mg/kg BW/day) |
| Compound A-2 | MF containing 0.005% of Compound A (Equivalent to 6.25 mg/kg BW/day) |
| Compound A-3 | MF containing 0.05% of Compound A (Equivalent to 62.46 mg/kg BW/day) |

MF: powder feed for raising mice and rats (MF) (manufactured by Oriental Yeast Co., Ltd.).
Compound A: (3S,8aS)-3-isobutylhexahydropyrrolo[1,2-a]pyrazine-1,4-dione (Compound 1 as above)
BW: Body Weight

[Results]

FIG. 4 shows the transition of the light period activity of rats after the phase advance. The horizontal axis represents the number of days elapsed since phase advance, the vertical axis represents the activity level in the light period (12 hours), and the activity level shows the mean value±standard error. For pre 3 days, the mean value of the light period activity level during the 3-day pre-administration period was shown.

From the shape of the graphs, it is shown that the activity level rises after the phase advance, and returns to the activity level before the phase advance with the passage of days.

As shown in FIG. 4, there was a particularly noticeable rise in the activity level in the light period on Day 1 and Day 2. In order to confirm the effect of Compound A on the activity level of Day 1 and Day 2 during the light period, Dunnett test with mixed model for repeated measures method was carried out. The Compound A-3 group showed a tendency to suppress the activity level in compared with the Control group (P=0.0978). Compound A-2 group significantly inhibited the activity level in compared with the Control group (P=0.0481). From these facts, it was suggested that Compound A suppresses sleep disturbance by phase advance during the light period from Day 1 to Day 2.

FIG. 5 shows the activity level of rats on Day 1, light period (12 hours) after the phase advance. The horizontal axis represents each group, the vertical axis represents the activity level in the light period (12 hours), and the activity level was the average value±standard error.

A group comparison was done by Dunnett test. As a result, the Compound A-3 group tended to suppress the activity level in compared with the Control group (P=0.0536), and the Compound A-2 group significantly suppressed the activity level in compared with the Control group (P=0.016). From these facts, it was suggested that. Compound A suppresses deterioration of sleep due to phase advance in the light period (12 hours) on Day 1.

As described above, both FIGS. 4 and 5 show significant difference after the phase advance in the early light period where the activity level is most likely to be disturbed. Therefore, it was suggested that Compound A improves sleep quality.

Example 3

Method Described in Wada T, et al., Brain Res Bull. 2006; 69: 388-92

An electrode for EEG is implanted in the brain of an 8-week-old male Wistar rat, and a recovery period is set for 1 week after surgery. After that, habituation to brush stimulation (sleep deprivation stimulus) is performed for 2-3 days. On test days, while monitoring EEG data, if non-REM sleep is detected, the rat is stimulated with a brush to prevent non-REM sleep. The effect of test drug on the influence of prevention of Non-REM sleep is examined.

Example 4

Method Described in Miyazaki K. et al., PLoS One. 2013; 8: e55452.

Male C3H-HeN mice aged 8 to 15 weeks old are subjected to stress by changing breeding on paper flooring in a cage with a rotating basket to that in 1.5 cm water-immersed state at room temperature on Day 1 of the test. In this state, the mice become to live on a rotating basket in order to avoid water immersion. The sleep/wakefulness of mice are evaluated by monitoring the activity status of the mice with the movement of the rotating basket. If evaluated after 7 days as a load, the evaluation in EEG and the evaluation by activity level will be similar.

Example 5

Method Described in Sei H. et al., Life Sci. 2003; 73: 53-59.

Male Wistar rats aged 10 to 12 weeks old are raised for 1 to 7 days after the change of the light/dark cycle of 12-hour dark period/12-hour light period to the light/dark cycle of 4-hour dark period/12-hour light period. For these animals, it is possible to assess the body temperature rhythm by installing a telemetry type thermometer in the abdominal cavity in advance. It is also possible to detect the modulation of body temperature rhythm and to assess the influence on plasma cortisol concentration and hippocampal BNDF protein mass, caused by changing the light/dark cycle.

Sequence Listing Free Text

The base sequence represented by SEQ ID NO: 1 is a base sequence of HSP70 forward primer.
The base sequence represented by SEQ ID NO: 2 is a base sequence of HSP70 reverse primer.
The base sequence represented by SEQ ID NO: 3 is a base sequence of beta 2 microglobulin forward primer.
The base sequence represented by SEQ ID NO: 4 is a base sequence of beta 2 microglobulin reverse primer.

The invention claimed is:

1. A method for improving sleep, which comprises administrating to a subject a combination of the following (a) to (c):

(a) (3S,8aS)-3-isobutylhexahydropyrrolo[1,2-a]pyrazine-1,4-dione (Cyclo(L-Leu-L-Pro))

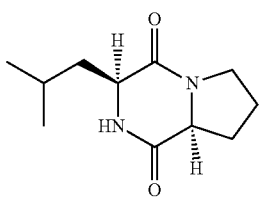

or a salt thereof, (b) (3S,8aS)-3-benzylhexahydropyrrolo[1,2-a]pyrazine-1,4-dione (Cyclo(L-Phe-L-Pro))

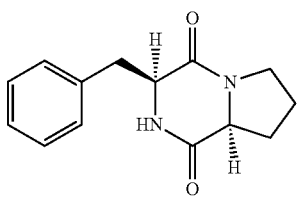 [SMILES: O=C1N[C@@H](Cc2ccccc2)C(=O)N2CCC[C@@H]12]

or a salt thereof, and (c) (3S,8aS)-3-(4-hydroxybenzyl)hexahydropyrrolo[1,2-a]pyrazine-1,4-dione (Cyclo(L-Tyr-L-Pro))

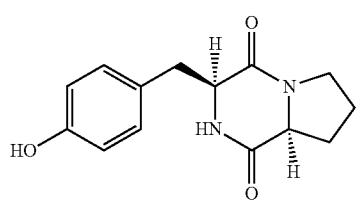 [SMILES: O=C1N[C@@H](Cc2ccc(O)cc2)C(=O)N2CCC[C@@H]12]

or a salt thereof,
wherein the daily dose of the Cyclo(L-Leu-L-Pro) is 10 µg-400 mg,
the daily dose of the Cyclo(L-Phe-L-Pro) is 5µg-300 mg, and
the daily dose of the Cyclo(L-Tyr-L-Pro) is 5 µg-600 mg,
wherein the subject is selected from the group consisting of subjects who have subjective dissatisfaction with sleeping feeling selected from the group consisting of shallow asleep, insufficient sleep feeling when getting up, poor sleep, insufficient deep sleep feeling, bad dreaming, and unrecovered fatigue;
subjects who want to improve sleep quality because they are feeling fatigue;
subjects who feels disorder of autonomic nerve;
subjects who are stressed in everyday life; and
subjects with the purpose selected from the group consisting of maintaining good sleep, preventing sleep disorders, improving sleep quality, autonomic nerve-adjusting activity, and anti-stress activity.

2. The method according to claim 1, wherein the compounds or salts thereof are administrated to the subject in the form of a pharmaceutical composition, or food and beverage composition.

* * * * *

SEQUENCE LISTING

<160> NUMBER OF SEQ ID NOS: 4

<210> SEQ ID NO 1
<211> LENGTH: 24
<212> TYPE: DNA
<213> ORGANISM: Artificial Sequence
<220> FEATURE:

```
<223> OTHER INFORMATION: Synthetic oligonucleotide primer, HSP70 forward
      primer

<400> SEQUENCE: 1
gcatttccta gtatttctgt ttgt                                              24

<210> SEQ ID NO 2
<211> LENGTH: 23
<212> TYPE: DNA
<213> ORGANISM: Artificial Sequence
<220> FEATURE:
<223> OTHER INFORMATION: Synthetic oligonucleotide primer, HSP70 reverse
      primer

<400> SEQUENCE: 2
aatagtcgta agatggcagt ata                                               23

<210> SEQ ID NO 3
<211> LENGTH: 19
<212> TYPE: DNA
<213> ORGANISM: Artificial Sequence
<220> FEATURE:
<223> OTHER INFORMATION: Synthetic oligonucleotide primer, beta 2
      microglobulin forward primer

<400> SEQUENCE: 3
tagctgtgct cgcgctact                                                    19

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide primer, beta 2
      microglobulin reverse primer

<400> SEQUENCE: 4
agtgggggtg aattcagtgt                                                   20
```